United States Patent
Sauter et al.

(10) Patent No.: US 11,478,246 B2
(45) Date of Patent: Oct. 25, 2022

(54) CLIP APPLICATOR

(71) Applicant: Aesculap AG, Tuttlingen (DE)

(72) Inventors: Wolfgang Sauter, Renquishausen (DE); Thomas Pleil, Bad Dürrheim (DE)

(73) Assignee: Aesculap AG, Tuttlingen (DE)

( * ) Notice: Subject to any disclaimer, the term of this patent is extended or adjusted under 35 U.S.C. 154(b) by 16 days.

(21) Appl. No.: 17/048,212

(22) PCT Filed: Apr. 18, 2019

(86) PCT No.: PCT/EP2019/060199
§ 371 (c)(1),
(2) Date: Oct. 16, 2020

(87) PCT Pub. No.: WO2019/202131
PCT Pub. Date: Oct. 24, 2019

(65) Prior Publication Data
US 2021/0161530 A1    Jun. 3, 2021

(30) Foreign Application Priority Data

Apr. 19, 2018   (DE) ..................... 10 2018 109 427.2

(51) Int. Cl.
*A61B 17/10* (2006.01)
*A61B 17/128* (2006.01)
(Continued)

(52) U.S. Cl.
CPC ............ *A61B 17/10* (2013.01); *A61B 17/128* (2013.01); *A61B 17/2816* (2013.01);
(Continued)

(58) Field of Classification Search
CPC ........ A61B 17/2833; A61B 2017/2946; A61B 17/10; A61B 17/128; A61B 17/2816;
(Continued)

(56) References Cited

U.S. PATENT DOCUMENTS 3,777,760 A   12/1973 Essner
5,876,420 A * 3/1999 Noll .................... A61B 17/0483
                                                        606/208
(Continued)

FOREIGN PATENT DOCUMENTS

DE   29800876 U1   3/1998
DE   10137915 A1   2/2003
(Continued)

OTHER PUBLICATIONS

German Search Report received in Application No. 10 2018 109 427.2 dated Feb. 26, 2019, 19 pages.
(Continued)

*Primary Examiner* — Shaun L David
*Assistant Examiner* — Mitchell Brian Hoag
(74) *Attorney, Agent, or Firm* — Christopher A. Rothe; Culhane Meadows, PLLC

(57) ABSTRACT

A surgical gripping/holding instrument having two instrument branches which are coupled pivotably with respect to one another. Each branch has a distal gripping/holding portion, a proximal instrument actuating portion, and an intermediate region which connects the distal and proximal portions preferably integrally, and having an instrument lock, of which the locking elements which can be brought into latching engagement with one another are arranged or formed on the instrument branches. The actuation of the instrument for opening and closing is functionally separated from actuation of the instrument for locking and unlocking the instrument by the positioning of the instrument lock in the intermediate region of the instrument. Therefore, each actuation can be carried out individually.

14 Claims, 3 Drawing Sheets

(51) Int. Cl.
*A61B 17/28* (2006.01)
*A61B 17/00* (2006.01)

(52) U.S. Cl.
CPC .............. *A61B 17/2833* (2013.01); *A61B 2017/00477* (2013.01); *A61B 2017/00862* (2013.01)

(58) Field of Classification Search
CPC ...... A61B 2017/00477; A61B 17/0483; A61B 2017/0488; A61B 2017/1125; A61B 17/22031; A61B 17/44
See application file for complete search history.

(56) References Cited

U.S. PATENT DOCUMENTS

| | | | |
|---|---|---|---|
| 6,066,159 A | 5/2000 | Bergstrom | |
| 6,096,059 A * | 8/2000 | Kuzma | A61B 17/29 |
| | | | 606/208 |
| 6,517,554 B1 * | 2/2003 | Zhu | A61B 17/30 |
| | | | 606/205 |
| 9,888,934 B2 * | 2/2018 | Storz | A61B 17/29 |
| 2002/0077649 A1 * | 6/2002 | Lasner | A61B 17/2841 |
| | | | 606/174 |
| 2006/0149315 A1 | 7/2006 | Kebel et al. | |
| 2010/0318104 A1 * | 12/2010 | Lazic | A61B 17/2812 |
| | | | 606/142 |
| 2018/0153535 A1 * | 6/2018 | Lasner | A61B 17/06061 |
| 2021/0213599 A1 * | 7/2021 | Mazzeo | A61B 17/3201 |

FOREIGN PATENT DOCUMENTS

| | | |
|---|---|---|
| DE | 60317702 | 10/2008 |
| DE | 202010008512 U1 | 11/2010 |

OTHER PUBLICATIONS

International Search Report received in Application No. PCT/EP2019/060199 dated Aug. 16, 2019, 4 pages.

* cited by examiner

CLIP APPLICATOR

CROSS-REFERENCE TO RELATED APPLICATIONS

This application is the United States national phase of International Application No. PCT/EP2019/060199, filed Apr. 18, 2019, which claims the benefit of priority of German Application No. 10 2018 109 427.2, filed Apr. 19, 2018. The contents of International Application No. PCT/EP2019/060199 and German Application No. 10 2018 109 427.2 are incorporated by reference herein in their entireties.

FIELD

The present invention relates to a surgical forceps/gripping instrument of the scissors or tweezers type and in particular to a clip applicator for holding/gripping/handing over a tissue clip, preferably an aneurysm clip.

BACKGROUND

When handing over or transferring a tissue/aneurysm clip, surgeons want a lock on the clip applicator used for this purpose that ensures that the clip does not fall out of the applicator during transfer, even if the clip applicator's holding/actuating grips are briefly released. Such a lock is intended to prevent the clip from being lost/falling off, but must not irritate or unduly hinder the surgeon during the surgical procedure.

From the prior art, surgical holding/gripping instruments of the scissors or tweezers type are generally known, which are equipped with so-called rotation stops, which are usually arranged at the proximal end (actuating portion) of the holding/gripping instrument and consist of a slide track on the side of one branch and a rotation cam on the side of the other branch, which is movably mounted on the other branch. When the two branches are pressed together in the area of the actuating portion of the instrument, the rotation cam engages in the slide track at its entrance, which has an undercut in the form of a concave curve into which the rotation cam engages when the two branches are detached/released for the first time, thereby holding the instrument in a closed state. If the two branches are then actuated again (second time), the rotation cam moves along the slide track from the concavely curved undercut towards the exit of the slide track and finally releases the two branches.

Another construction variant provides metal sheets which are mounted in an exposed position on each of the branches and which, starting from an initial angular position X of the branches, run up against each other, engage behind each other at an angular position of, for example, X−5° and are thus latched in place, and are run past at an angular position of, for example, X−10°.

A disadvantage of this solution is that the entire angular range X−10° has to be passed also during the application process of the clip. The springback of the lock that occurs when passing is perceived as unpleasant and causes irritation during the application process.

SUMMARY

In view of the aforementioned problem, it is the object of the present invention to provide a surgical gripping/holding instrument, preferably of the scissors/of the forceps type or tweezers type with a lock/circulation lock, in which irritations caused by the lock are reduced or prevented.

The core of the present invention therefore consists of arranging the (circulation) lock in a region between the gripping/holding portion (distal effector portion of the instrument) and the (proximal, manual) actuating portion of the surgical instrument, and of designing the instrument branches in this intermediate region in such a way that the lock cannot be brought into the locking state when the instrument is (manually) actuated exclusively at the actuating portion of the instrument provided for this purpose. According to the invention, this locking state can only be achieved by actuating the instrument preferably in addition to the actuation at the actuating portion provided for this purpose in the intermediate region (located outside the actuating portion) (which connects the gripping/holding portion with the actuating portion). More precisely, it is provided that the intermediate regions are the exclusive actuating elements for engaging and disengaging the instrument lock.

For the sake of clarification, it should be mentioned here that the (manual) actuating portions of the instrument branches are the instrument actuating portions, with which the instrument branches can be pivoted relative to each other, for example by the user, i.e. the instrument can be opened and closed at these instrument actuating portions or respectively can be actuated in its opening and closing direction. In other words, instrument actuation is to be understood in the sense of opening and closing the instrument. The instrument is actuated by means of the (proximal) instrument actuating portions. The instrument lock is a releasable instrument lock.

The surgical gripping/holding instrument according to the invention has two instrument branches that can be moved relative to each other and which are pivotably coupled to each other in the manner of scissors/forceps or tweezers. These two branches form the holding/gripping portion at their respective distal end portion and the preferably manual actuating portion at their proximal end portion, for example an instrument handle for opening and closing the instrument at the gripping/holding portion of the branches (hereinafter referred to as instrument actuating portion). The holding/gripping portion and the actuating portion of each branch are connected to each other, preferably integrally, by the intermediate region, in which, for example in the case of a scissors/forceps design, a hinge joint is located, by means of which the two branches are pivotably coupled to each other. The (branch) lock, i.e. the locking elements to be brought into locking/latching engagement with each other, preferably of a known design (cams, slide tracks, plates, etc.), is arranged in the intermediate region, in the case of the scissors/forceps design, preferably with respect to the hinge joint on the side of the actuating portions.

In this case, the branches in their respective intermediate regions (outside the respective actuating portions for opening and closing the instrument) are shaped according to the invention, preferably arcuate, in such a way that the opposing locking elements of the instrument lock remain disengaged if the instrument is completely actuated (i.e. up to the maximum possible/permissible actuating position/actuating state, in particular closed state/closed position) only at the actuating portions (instrument handle) of the branches (as prescribed) for grasping/holding an object/tissue, in particular an aneurysm clip (opening and closing). The gripping/holding instrument according to the invention therefore forms a second actuating portion/actuating element (exclusively) for locking/unlocking or engaging/disengaging the instrument lock (hereinafter referred to as lock actuating portion), whereby the first (manual) actuation of the second actuating portion with the instrument actuating portion already actuated can bring the lock into the locked state without having to carry out further manipulations on the actuating state of the instrument actuating portion. If the instrument is to be opened again, the lock actuating portion has to be operated twice (without further manipulation of the instrument actuating portion) in order to release the lock (circulation lock) in a known manner and then the instrument actuating portion has to be released in order to open the instrument.

Functionally, the invention can thus be described in such a way that the actuation of the instrument for opening and closing is functionally separated from the actuation of the instrument for locking and unlocking the instrument (exclusively by the positioning of the lock in the intermediate region according to the invention) and can thus be performed individually (optional activation of the lock).

In particular, the instrument lock is engaged and disengaged by elastic deformation of the intermediate regions, in particular exclusively by elastic deformation of the intermediate regions.

The two locking elements preferably form a circulation lock. Especially preferably, the two locking elements move towards each other by means of a first actuation of the instrument lock in order to latch together, and move towards each other again by means of a second actuation of the instrument lock in order to disengage again.

Preferably, the two instrument branches form a gap between their respective intermediate regions (or actuating elements for engaging and disengaging the instrument lock) when the instrument is only actuated at the proximal actuating portions of the instrument branches up to a maximum possible actuating position, in particular (a maximum possible) closed position/closed state, for grasping/holding an object/tissue. When the instrument lock is actuated for the first time by applying pressure to the two intermediate regions in such a way that they move towards each other, the gap closes and the two opposite locking elements latch together. In particular, when the instrument lock is actuated a second time by applying pressure to the two intermediate regions so that they move towards each other, the two locking elements are released from the latching engagement.

Especially preferably, the locking elements in the intermediate regions of the instrument branches are arranged in such a way that they can latch together and in particular be released by a sideways movement perpendicular to the opening/closing direction of the instrument branches, preferably perpendicular to the pivot plane of the instrument branches, or by a movement in the opening/closing direction of the instrument branches, preferably in the pivot plane of the instrument branches.

BRIEF DESCRIPTION OF THE DRAWING FIGURES

The invention is further explained in the following on the basis of a preferred embodiment with reference to the accompanying figures. These show:

DETAILED DESCRIPTION

Figure 1:
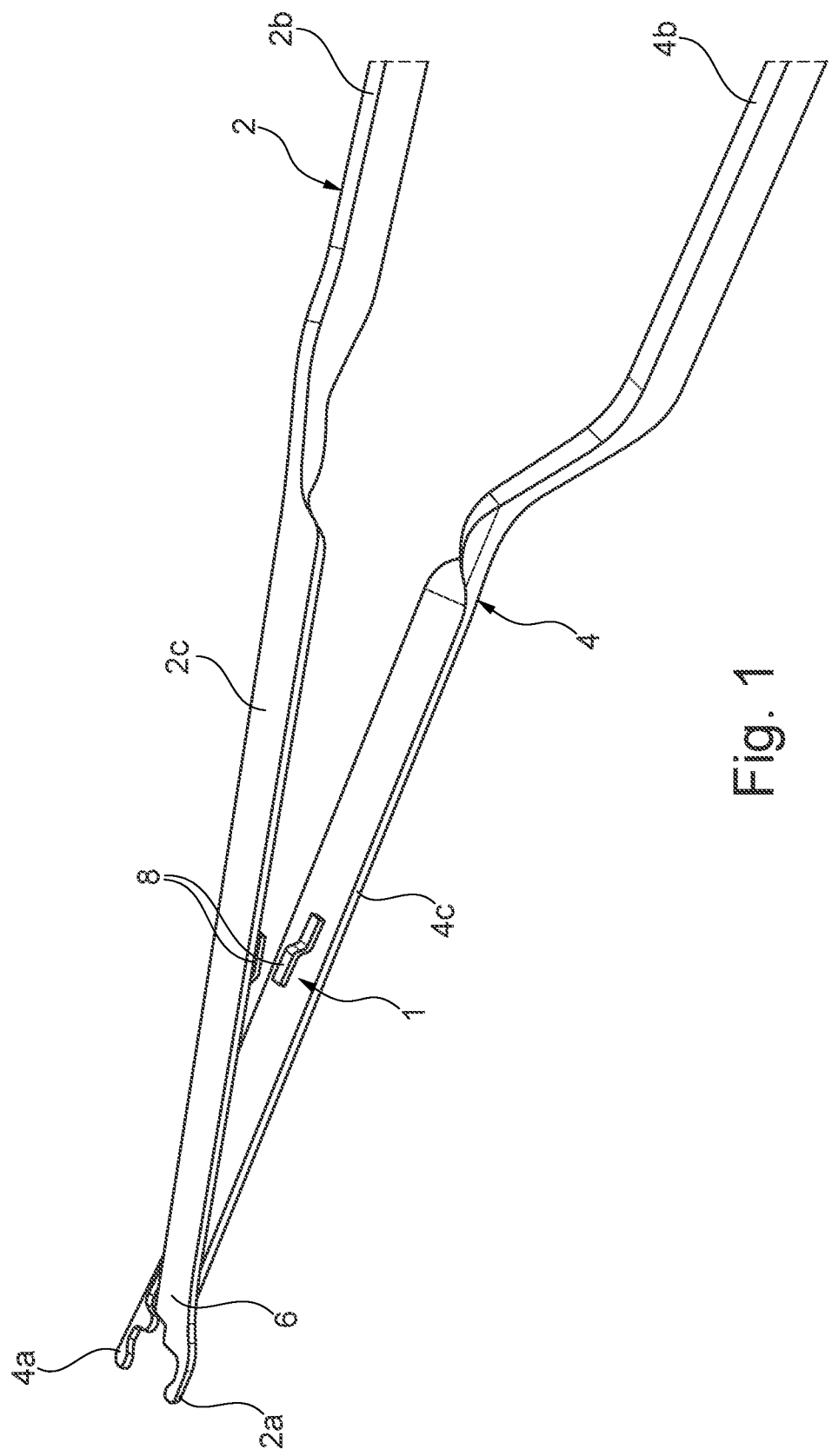
FIG. 1 shows a surgical holding/gripping instrument preferably of the forceps type in particular an aneurysm clip applicator according to a preferred embodiment of the invention in an unactuated/open state.
Figure 2:
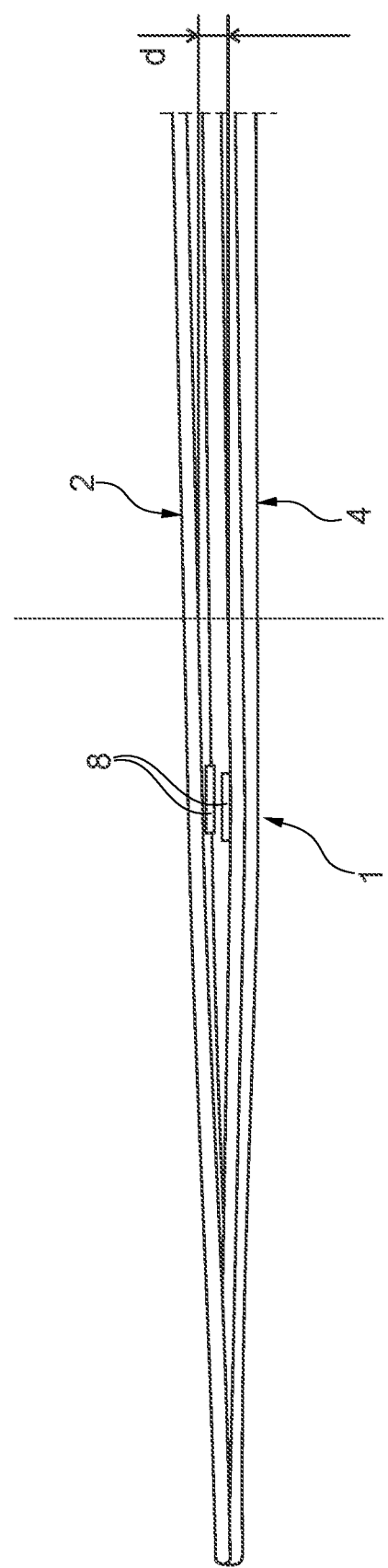
FIG. 2 shows the surgical holding/gripping instrument according to FIG. 1 in an actuated/closed state with the instrument lock being unactuated/unlocked.
Figure 3:
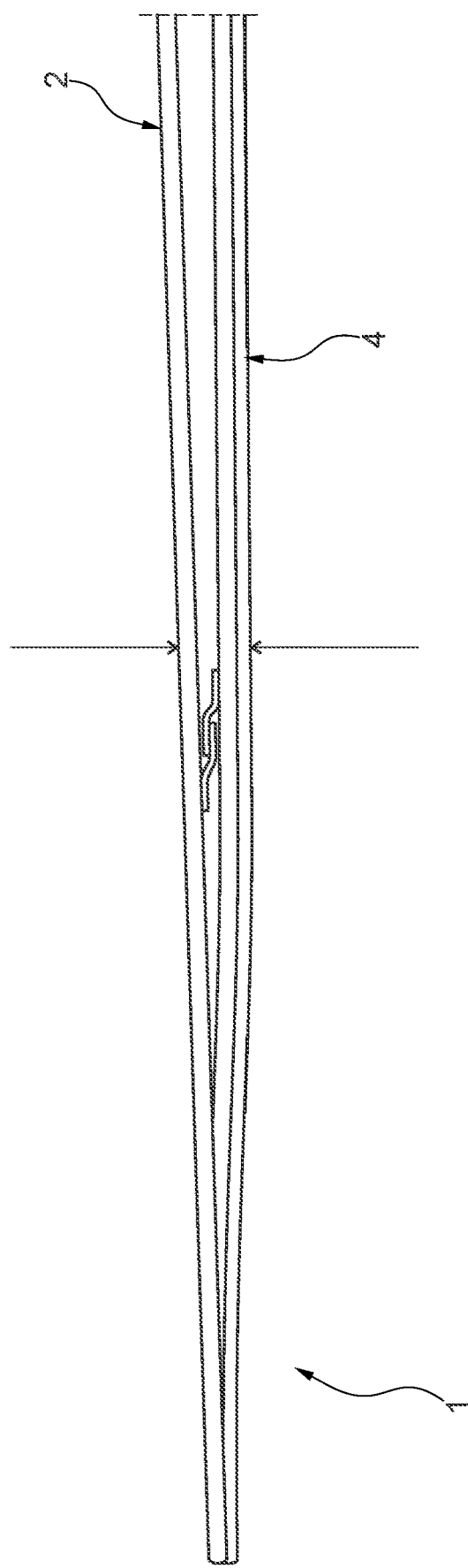
FIG. 3 shows the surgical holding/gripping instrument according to FIG. 2 in an actuated/closed state with the (connected) instrument lock being actuated/locked.

According to FIG. 1, the surgical gripping/holding instrument 1 of the preferred embodiment of the present invention is an aneurysm clip applicator of the forceps/scissors type with two preferably bar-shaped instrument branches 2, 4, which each form a distal holding/gripping portion 2$a$, 4$a$, a proximal instrument actuating portion 2$b$, 4$b$ and an intermediate region 2$c$, 4$c$ which couples/connects the distal holding/gripping portion 2$a$, 4$a$ and the proximal instrument actuating portion 2$b$, 4$b$ integrally. In the present embodiment, the two instrument branches 2, 4 are pivotably coupled to each other via a swing hinge, preferably in the form of a hinge pin or bolt 6, which is arranged in the intermediate region 2$c$, 4$c$, preferably at the distal end of the intermediate region 2$c$, 4$c$, and for this purpose is inserted into a through-hole (not shown in greater detail) at each of the instrument branches 2, 4.

At this point it shall be pointed out that the surgical gripping/holding instrument can also be designed in the manner of a pair of tweezers, likewise with two instrument branches, each of which defines a distal holding/gripping portion, a proximal instrument actuating portion, and an intermediate region coupling the distal holding/gripping portion as well as the proximal instrument actuating portion integrally, wherein in this case, however, the two instrument branches are coupled to each other via a spring hinge (leaf spring portion) at the respective proximal end of the instrument actuating portions.

As can be clearly seen from FIG. 1, the holding/gripping portion 2$a$, 4$a$ of each instrument branch 2, 4 can be designed and prepared to grip and hold an implant, for example an aneurysm clip, in mutual interaction. However, it is also conceivable to optimize the holding/gripping portions 2$a$, 4$a$ according to the invention for gripping and holding another surgical object, e.g. a needle or the like or patient tissue.

The proximal instrument actuating portions 2$b$, 4$b$ are provided and adapted to be grasped manually, i.e. with the hand, and to be moved or pivoted relative to each other (towards each other) to close the instrument 1 (the distal gripping/holding portions 2$a$, 4$a$). For (maximum) opening and (maximum) closing of the surgical instrument 1 according to the invention, a predetermined (maximum) movement path or pivot angle of the branches 2, 4/proximal instrument actuating portions 2$b$, 4$b$ is necessary or provided, which can be limited, for example, by stops in the opening and/or closing direction (not shown further).

Finally, the surgical instrument 1 is equipped with an instrument lock 8, which is positioned according to the invention in the intermediate region 2$c$, 4$c$ of each instrument branch 2, 4, i.e. outside the instrument actuating portions 2$b$, 4$b$ and outside the gripping/holding portions 2$a$, 4$a$ of each instrument branch 2, 4. Preferably, the instrument lock 8 is positioned in the intermediate region 2$c$, 4$c$ between the proximal actuating portions 2$b$, 4$b$ and the hinge (pin) 6.

The instrument lock 8 is constructed according to a known design, i.e. it essentially consists of two locking elements which can be latched together, for example in the form of metal sheets forming undercuts, latching cams and/or slide tracks, which are arranged opposite each other and facing each other on the instrument branches 2, 4 in such a way that when the lock 8 is actuated for the first time by moving the two locking elements towards each other, they latch together and thus lock the instrument branches 2, 4 or respectively the instrument 1 in the closed state, and when the lock 8 is actuated a second time (e.g. also by moving the two locking elements towards each other), they are released from each other and thus release the instrument branches 2, 4 or respectively the instrument 1 again for opening it.

At this point, it shall be pointed out that the instrument lock 8 can have any design in accordance with the prior art. For example, a guide link can be arranged on one of the branches 2, 4 and a rotation cam can be hinged on the opposite branch 4, 2, resulting in an instrument lock 8 of the rotation design. However, it is also possible to equip each instrument branch 2, 4 with a preferably hook-shaped metal sheet, which are arranged in such a way that they can be locked together and released again by a lateral movement (perpendicular to the opening/closing direction) of the instrument branches 2, 4 (laterally offset lock).

According to the invention, the intermediate region 2c, 4c of at least one branch 2, 4, at least in sections thereof, is shaped such that the instrument lock 8 or its locking elements cannot be latched if the surgical instrument 1 is actuated exclusively at its proximal instrument actuating portions 2b, 4b up to the maximum actuating position. Specifically, the intermediate regions 2c, 4c of at least one, preferably both, instrument branches 2, 4 are designed, for example, in an arc shape, in such a way that, when exclusively the proximal actuating portions 2b, 4b are actuated up to their maximum actuating/closed position, a gap d results/remains between the instrument branches 2, 4, at least at the intermediate regions 2c, 4c, said gap d being dimensioned in such a way that the two locking elements of the instrument lock 8 facing each other cannot be brought/do not come into latching engagement.

In accordance with the invention, the intermediate region 2c, 4c of at least one, preferably each instrument branch 2, 4 forms a locking actuating portion in addition to the proximal instrument actuating portion 2b, 4b, which can be actuated separately from the proximal instrument actuating portion 2b, 4b (exclusively) for optionally locking and releasing the instrument lock 8 (with the instrument already closed/at maximum actuation/closed position of the proximal instrument actuating portions 2b, 4b).

Consequently, the intermediate region 2c, 4c of at least one/each instrument branch 2, 4 may have an actuating surface/actuating structure on one side of the branch, which also serves as a position marker for the application of pressure/force directly to the intermediate region 2c, 4c and may be ergonomically adapted to a finger/thumb, for example. This means that the surgical gripping/holding instrument 1 or its instrument branches 2, 4 according to the invention each has/have two actuating portions, i.e. the proximal instrument actuating portion 2b, 2c exclusively for closing (and opening) the instrument 1 and the locking actuating portion arranged in/formed by the intermediate region 2c, 4c exclusively for locking and/or releasing the instrument lock 8.

The functionality of the surgical gripping/holding instrument according to the invention can be summarized as follows:

First of all, the instrument 1 according to the invention can be closed manually at the proximal instrument actuating portions 2b, 4b like an instrument of this type known from the prior art by pivoting the branches 2, 4, which are coupled in a relative pivotable manner, towards each other at their proximal instrument actuating portions 2b, 4b until a maximum closed position is reached, if desired. Since the locking elements of the instrument lock 8 do not come into latching engagement during this instrument actuation, because they maintain a distance to each other as a result of the design of the intermediate regions 2c, 4c according to the invention as well as the special positioning of the lock 8 in the intermediate region 2c, 4c of the branches 2, 4, the instrument 1 can simply be opened again by releasing the actuating portions 2b, 4b.

In order to optionally lock the instrument 1 in the closed position, the lock has to be activated by (additionally) actuating the locking actuating portion/intermediate region 2c, 4c. This means that after actuating the proximal instrument actuating portions 2b, 4b in order to close the instrument 1, the lock 8 is additionally actuated by moving the intermediate regions 2c, 4c towards each other by directly applying force/pressure to them in order to close the gap d remaining between them when exclusively actuating the proximal instrument actuating portions 2b, 4b and thus to lock the two opposite locking elements.

If the instrument that has been latched in this way is to be opened again, the intermediate regions 2c, 4c have to be moved directly towards each other again (with the proximal instrument actuating portions 2b, 4b in their maximum closed position, if necessary) in order to bring the two locking elements out of latching engagement, whereupon the proximal instrument actuating portions 2b, 4b can be released to open instrument 1.

This has the following advantages over the well-known instruments of this genre:

- No haptic irritation of the surgeon during the application process (opening and closing);
- Facilitated, targeted latching of the instrument lock;
- Less susceptible to interference (no unintentional unlocking when the proximal instrument actuating portions are accidentally actuated, no switching errors due to bent locking elements);
- Simplified and safe cleaning;
- Simplified manufacture (no assembly/adjustment);
- Reduced manufacturing costs;
- Flatter learning curve than with instruments of known design;
- Tamper-proof;
- Optional connectability of the lock is given.

The invention claimed is:

1. A surgical gripping or holding instrument having two instrument branches which are coupled pivotably with respect to each other and which each have a distal gripping or holding portion, a proximal instrument actuating portion and an intermediate region which connects the distal gripping or holding portion and the proximal instrument actuating portion, and having an instrument lock whose locking elements which can be brought into latching engagement with each other are arranged or formed on the instrument branches, wherein actuation of the instrument for opening and closing and actuation of the instrument for locking and unlocking the instrument are functionally separated by a positioning of the instrument lock in the intermediate regions of the instrument branches and thus can be carried out individually, wherein the intermediate regions of the instrument branches form exclusive actuating elements for engaging and disengaging the instrument lock, wherein the intermediate region of at least one of the instrument branches is formed such that when the proximal instrument actuating portions are actuated up to their maximum actuating positions or closing positions in an opening and closing direction, a gap remains between the two instrument branches, wherein the gap only closes and the locking elements of the instrument lock come only in latching engagement by actuating an actuating structure or an actuating surface in the intermediate region, which actuating structure or actuating surface is arranged distally with respect to the proximal instrument actuating portions, and wherein the actuating structure or the actuating surface in the intermediate region is actuable such that the instrument branches move towards each other in a direction perpendicular to the opening and closing direction, in order to close the gap and bring the locking elements of the instrument lock in latching engagement.

2. The surgical gripping or holding instrument according to claim 1, wherein the instrument branches are bar shaped.

3. The surgical gripping or holding instrument according to claim 1, wherein a latching/locking state of the instrument lock can only be achieved by actuating the instrument in addition to directly actuating the proximal instrument actuating portions, in the intermediate regions located outside the proximal instrument actuating portions and connecting the distal gripping or holding portions to the proximal instrument actuating portions.

4. The surgical gripping or holding instrument according to claim 3, wherein the instrument branches which are movable relative to each other are pivotably coupled to each other, and the proximal instrument actuating portions each can be applied with manual force and form an instrument handle for opening and closing the instrument, wherein a hinge joint is provided, via which the instrument branches are pivotably coupled to each other, wherein the instrument lock is arranged in the intermediate region on the side of the proximal instrument actuating portions relative to the hinge joint.

5. The surgical gripping or holding instrument according to claim 1, wherein the instrument branches in their respective intermediate regions outside the proximal instrument actuating portions are shaped for opening and closing the instrument, such that the opposite locking elements of the instrument lock remain disengaged when the instrument is actuated only at the proximal instrument actuating portions of the instrument branches up to a maximum possible actuating position for gripping or holding an object or tissue.

6. The surgical gripping or holding instrument according to claim 1, wherein engagement and disengagement of the instrument lock is affected by elastic deformation of the intermediate regions.

7. The surgical gripping or holding instrument according to claim 1, wherein the two locking elements form a circulation lock, the two locking elements moving towards each other in order to latch together by a first actuation of the instrument lock, and the two locking elements moving towards each other again by a second actuation of the instrument lock in order to disengage from each other again.

8. The surgical gripping or holding instrument according to claim 1, wherein the two instrument branches form a gap between their respective intermediate regions when the instrument is actuated only at the proximal instrument actuating portions of the instrument branches up to a maximum possible actuating position for gripping or holding an object or tissue, and by actuating the instrument lock for a first time by applying force to the intermediate regions in such a way that the intermediate regions move towards each other, the gap closes, and the locking elements latch together, and by actuating the instrument lock a second time by applying force to the intermediate regions in such a way that they move towards each other, the locking elements are released from latching engagement.

9. The surgical gripping or holding instrument according to claim 1, wherein the locking elements in the intermediate regions of the instrument branches are each arranged in such a way that they can be latched together and released again by a lateral movement perpendicular to the opening or closing direction of the instrument branches or by a movement in the opening or closing direction of the instrument branches.

10. The surgical gripping or holding instrument according to claim 1, wherein for each instrument branch:
the distal gripping or holding portion is arranged at a distal end of the surgical gripping or holding instrument and is configured for grasping or holding an object or tissue,
the intermediate region is separate from the distal gripping or holding portion and arranged proximally from the distal gripping or holding portion, and
the proximal instrument actuating portion is separate from the intermediate region, is arranged proximally from the intermediate region, is manually actuatable by a user, and is configured to pivot the instrument branches relative to each other.

11. The surgical gripping or holding instrument according to claim 10, wherein the instrument branches are pivotally coupled via a swing hinge, wherein, for each instrument branch, the distal gripping or holding portion is arranged distally with respect to the swing hinge, wherein the swing hinge is arranged distally with respect to the intermediate region, and wherein the intermediate region is arranged distally with respect to the proximal instrument actuating portion.

12. The surgical gripping or holding instrument according to claim 1, wherein the instrument branches are coupled pivotally via a swing hinge, and the locking elements of the instrument lock are located proximally with respect to the swing hinge and distally with respect to the proximal instrument actuating portions.

13. The surgical gripping or holding instrument according to claim 1, wherein the surgical gripping or holding instrument comprises first actuating portions formed by the proximal instrument actuating portions, the first actuating portions being provided and configured exclusively for closing and opening two instrument branches of the surgical gripping or holding instrument, and second actuating portions being formed by locking actuating portions provided separately from and distally with respect to the first actuating portions.

14. The surgical gripping or holding instrument according to claim 13, wherein the locking actuating portions are actuated and the locking elements of the instrument lock are brought into latching engagement by moving the intermediate regions towards each other in a direction perpendicular to an opening and closing direction of the two instrument branches.

* * * * *